United States Patent [19]

Corbin et al.

[11] Patent Number: 5,344,989

[45] Date of Patent: Sep. 6, 1994

[54] ZEOLITE ZK-5 CATALYST FOR CONVERSION OF METHANOL AND AMMONIA TO MONOMETHYLAMINE AND DIMETHYLAMINE

[75] Inventors: David R. Corbin, West Chester, Pa.; Stephan Schwarz, Newark, Del.

[73] Assignee: E. I. Du Pont de Nemours and Company, Wilmington, Del.

[21] Appl. No.: 77,578

[22] Filed: Jun. 15, 1993

[51] Int. Cl.$^5$ .......................................... C07C 209/16
[52] U.S. Cl. ................................... 564/479; 564/474
[58] Field of Search ................................. 564/479, 474

[56] References Cited

U.S. PATENT DOCUMENTS

| | | | |
|---|---|---|---|
| 3,247,195 | 4/1966 | Kerr | 260/242 |
| 3,720,753 | 3/1973 | Robson | 423/329 |
| 3,904,738 | 9/1975 | Robson | 423/328 |
| 4,602,112 | 7/1986 | Gier et al. | 564/474 |
| 4,683,334 | 7/1987 | Bergna et al. | 564/474 |
| 4,752,596 | 6/1988 | Bergna et al. | 502/64 |
| 4,806,689 | 2/1989 | Gier et al. | 564/474 |
| 4,814,503 | 3/1989 | Abrams et al. | 564/474 |
| 4,994,249 | 2/1991 | Verduijn | 423/328 |
| 5,137,854 | 8/1992 | Segawa et al. | 502/64 |

OTHER PUBLICATIONS

R. D. Shannon et al., *Journal of Catalysis,* 115:79–85 (1989).
R. D. Shannon et al., *Journal of Catalysis,* 113:367–382 (1988).
F. J. Weigert, *Journal of Catalysis,* 103:20–29 (1987).
F. Fettin et al., *Chem. Eng. Technol.* 15:202–212 (1992).
M. Keane, Jr., et al., *Applied Catalysis,* 32:361–366 (1987).
J. L. Lievens, et al., *Zeolites,* 12: 690–697 (Jul./Aug. 1992).

*Primary Examiner*—Glennon H. Hollrah
*Assistant Examiner*—Scott C. Rand

[57] ABSTRACT

An improved process for production of monomethylamines and dimethylamines, wherein an acidic zeolite H—ZK-5 prepared from K,Sr—ZK-5 is used to increase selectivity of the reaction.

7 Claims, No Drawings

ZEOLITE ZK-5 CATALYST FOR CONVERSION OF METHANOL AND AMMONIA TO MONOMETHYLAMINE AND DIMETHYLAMINE

BACKGROUND OF THE INVENTION

This invention involves a process for making amines, specifically monomethylamine and dimethylamine, in which methanol and/or dimethylether and ammonia are contacted in the presence of a zeolite catalyst.

Methylamines are generally prepared in industrial quantities by continuous reaction of methanol and ammonia in the presence of a silica-alumina catalyst. The reactants are typically combined in the vapor phase, at temperatures in the range of 300° C. to 500° C., and at elevated pressures. Trimethylamine is the principal component of the resulting product stream, accompanied by lesser amounts of monomethylamine, and dimethylamine. From a commercial standpoint, the most valued product of the reaction is dimethylamine, in view of its widespread industrial use as a chemical intermediate. Accordingly, a major objective of those seeking to enhance the commercial efficiency of this process has been to improve overall yields of dimethylamine and monomethylamine, relative to trimethylamine. Among the approaches taken to meet this objective are recycling of trimethylamine, adjustment of the ratio of methanol to ammonia reactants and use of selected dehydrating or aminating catalyst species. Due to the commercial importance of the process, quite a number of patents and technical contributions to the literature have resulted. Those most relevant to the present invention are summarized below.

Gier et al., U.S. Pat. No. 4,602,112, disclose a process for producing dimethylamine comprising reacting methanol and/or dimethylether and ammonia in amounts sufficient to provide a C/N ratio from about 0.2 to about 1.5, at a temperature from about 250° C. to about 450° C., in the presence of a catalytic amount of an acidic H—ZK-5 zeolite derived from K, Cs—ZK-5 catalyst.

Gier et al., U.S. Pat. No. 4,806,689, disclose a process for producing dimethylamine, as described above, in the presence of a catalytic amount of an acidic zeolite rho.

Abrams et al., U.S. Pat. No. 4,814,503, disclose an improvement to Gier's '689 process (above) through the use of catalyst zeolite rho, zeolite ZK-5 or a combination thereof, calcined in the presence of steam and/or ammonia, which improves catalyst selectivity to dimethylamine and catalyst activity.

Kerr, U.S. Pat. No. 3,247,195, first discloses the composition and method of preparation of zeolite ZK-5, prepared from mixtures of oxides Na$_2$O, Al$_2$O$_3$, [(CH$_3$)$_2$(CH$_2$CH$_2$)$_3$N$_2$]O, SiO$_2$, and H$_2$O, and identified by its X-ray diffraction pattern.

Robson, U.S. Pat. No. 3,720,753, discloses a preparation of zeolite ZK-5 prepared from K and Cs. Robson, U.S. Pat. No. 3,904,738, discloses a preparation of zeolite rho.

Shannon et. al., Journal of Catalysis 115 (1989) describes the physical and catalytic properties of ZK-5 catalysts prepared by deep-bed and shallow-bed calcination techniques and the effect on selectivity.

Verduijn, U.S. Pat. No. 4,994,249, discloses a preparation of ZK-5 having a SiO$_2$/Al$_2$O$_3$ ratio of up to 10 prepared by the use of potassium and strontium in the synthesis gel, which was found to be useful as a catalyst in hydrocracking, reforming and for separations.

As the foregoing discussion suggests, new process improvements which suppress production of trimethylamine and optimize dimethylamine and monomethylamine yields are of significant interest to the chemical industry.

SUMMARY OF THE INVENTION

The present invention provides a process for producing dimethylamine (DMA) and monomethylamine (MMA) comprising contacting methanol and/or dimethylether and ammonia, in amounts sufficient to provide a carbon/nitrogen (C/N) ratio from about 0.2 to about 1.5 and at a reaction temperature from about 250° C. to about 450° C., in the presence of a catalytic amount of an acidic zeolite ZK-5, wherein the acidic zeolite ZK-5 has been prepared from K, Sr—ZK-5 rather than the more traditional K, Cs—ZK-5, and has yielded a much reduced selectivity to trimethylamine (TMA), and increased selectivity to DMA and MMA compared to the K, Cs—ZK-5. The K, Sr—ZK-5 derived catalyst can be calcined at a temperature from about 400° C. to about 700° C. to yield H—ZK-5; the preferred calcining conditions being 500° C. to 600° C. The preferred methylamine reaction conditions are a C/N ratio from 0.5 to 1.2, reaction temperatures from 300° C. to 400° C., reaction pressures from 10 to 500 psi (70–3000 kPa) and space time of 0.1 to 1.5 hrs.

The acidic form of the catalyst, H—ZK-5, used in methylamines synthesis is obtained by ion exchange with ammonium salts such as ammonium acetate or ammonium nitrate, followed by calcination. In preparing the catalyst, the ease of ion exchange, i.e. the number of exchanges needed to most completely remove the ions, was greatly enhanced by the use of K, Sr—ZK-5 rather than the traditional K, Cs—ZK-5. Six NH$_4$+ exchanges with NH$_4$NO$_3$ yield only 0.2 K/unit cell remaining in the K, Sr system, a vast improvement over K, Cs—ZK-5, which yielded 2.7 (K+Cs)/unit cell after twelve similar exchanges.

DETAILED DESCRIPTION OF THE INVENTION

Zeolites can be generically described as complex aluminosilicates characterized by a three-dimensional framework structure enclosing cavities occupied by ions and water molecules, all of which can move with significant freedom within the zeolite matrix. In commercially useful zeolites, the water molecules can be removed from or replaced within the framework without destroying its geometry. Zeolites can be represented by the following formula:

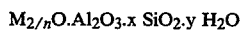

$$M_{2/n}O.Al_2O_3.x\ SiO_2.y\ H_2O$$

wherein M is a cation of valence n, x≧2 and y is a number determined by the porosity of the hydration state of the zeolite, generally from about 2 to 8. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

Zeolite structure consists of corner-linked tetrahedra with Al or Si atoms at centers of tetrahedra and oxygen atoms at corners. Such tetrahedra are combined in a well-defined repeating structure comprising various combinations of 4-, 5-, 6-, 8-, 10-and 12-membered rings. The resulting framework consists of regular channels and cages, which impart a useful pore structure catalysis. Pore dimensions are determined by the geometry of the aluminosilicate tetrahedra forming the zeolite channels or cages, with nominal openings of 0.26 nm for 6 rings, 0.40 nm for 8 rings, and 0.55 nm for 10 rings. Pore dimensions are critical to catalytic performance since this characteristic determines whether reactant molecules can enter the zeolite framework and which molecules can exit. In practice, it has been observed that very slight decreases in ring dimensions can effectively hinder or block movement of particular reactants or products within a zeolite structure.

The pore dimensions which control access to the interior of the zeolite are determined not only by the tetrahedra forming the pore opening, but also by the presence or absence of ions in or near the pore. In the case of zeolite A, for example, access can be restricted by monovalent ions, such as $Na^+$ or $K^+$, which are situated in or near 8-ring openings as well as 6-ring openings. Access is enhanced by divalent ions, such as $Ca^{2+}$, which are situated only in or near 6-rings. Thus K-A and Na-A exhibit effective pore openings of about 0.3 nm and 0.4 nm respectively, whereas Ca-A has an effective pore opening of 0.5 nm.

Useful references generally relating to zeolite structure and characterization include the following:

Meier et al., Atlas of Zeolite Structure Types (International Zeolite Assn. 1978);

Mumption, "Natural Zeolites" in Reviews in Minerology 14:1 (1977);

Smith, "Origin and Structure of Zeolites" in Zeolite Chemistry and Catalysis, ACS Monograph 171 (American Chemical Society, 1976).

General Characteristics of ZK-5

Zeolite K, Cs—ZK-5 is a synthetic zeolite first described by Robson, U.S. Pat. No. 3,720,753. The disclosure of this patent, which provides details regarding synthesis of the ZK-5 zeolite, is incorporated by reference herein. The structure of ZK-5 consists of truncated cuboctahedra linked by hexagonal prisms and enlarged double 8-rings with openings of 0.39 nm. ZK-5 zeolites can be characterized by the following formula:

$$(K,Cs)_{30}Al_{30}Si_{66}O_{192}$$

The present invention employs the method disclosed by Verduijn, U.S. Pat. No. 4,994,249, incorporated by reference herein, for preparation of ZK-5 using potassium and strontium. This zeolite can be characterized in the anhydrous state by the following formula:

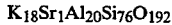

$$K_{18}Sr_1Al_{20}Si_{76}O_{192}$$

The cationic species $K^+$ and $Cs^+$ present in the Robson ZK-5, and $K^+$ and $Sr^{2+}$ in the Verduijn ZK-5, can be exchanged with $H^+$ or by conversion to an ammonium-exchanged form ($NH_4$—ZK-5) which is subsequently converted to an acid form by calcination at elevated temperatures.

Acid forms of zeolites can be prepared by a variety of techniques including ammonium exchange followed by calcination, direct exchange of alkali ions for protons using mineral acids or ion exchangers, and by introduction of polyvalent ions (for a discussion of acid sites in zeolites, see J. Dwyer, "Zeolite Structure Composition and Catalysis" in Chemistry and Industry, Apr. 2, 1984).

The acid sites produced are generally believed to be of the Bronsted (proton donating) type or of the Lewis (electron pair accepting) type. Bronsted sites are generally produced by deammoniation at low temperatures, exchange with protons, or hydrolysis of polyvalent cations. Lewis sites are believed to arise from dehydroxylation of the H-zeolites or from the presence of polyvalent ions. In the acidic zeolite catalysts of the present invention, Bronsted and/or Lewis sites can be present.

Catalyst Preparation

The present invention employs the method disclosed by Verduijn, U.S. Pat. No. 4,994,249, incorporated by reference herein, for preparation of ZK-5 using potassium and strontium. This ZK-5 catalyst was developed for use as a catalyst for hydrocracking, reforming and for separations. Its use in the production of methylamines yields, surprisingly, a greatly enhanced selectivity to MMA and DMA. Only methods involving coating the catalyst with a material such as tetramethoxysilane (Fetting et al., "Production of Methylamines over ZK-5 Zeolite Treated with Tetramethoxysilane", Chemical Engineering and Technology 15 (1992)), have produced such comparably low selectivity to TMA with increased selectivity to DMA and MMA.

Zeolite ZK-5 is synthesized in a K, Cs form substantially according to the procedure disclosed in Robson, U.S. Pat. No. 3,720,753, incorporated by reference herein.

Zeolite rho is synthesized in a Na, Cs form substantially according to the procedure of Robson, U.S. Pat. No. 3,904,738, the relevant disclosure of which is incorporated herein by reference.

In one method of preparing the H-form of each catalyst employed in the process of this invention, $K^+$ and $Sr^{2+}$, $K^+$ and $Cs^+$, or ($Na^+$ and $Cs^+$) ions are exchanged for $NH_4^+$ ions and the resulting $NH_4^+$ form deammoniated by calcination at 400° C. to 700° C. In the K, Cs form of ZK-5, more extensive exchange produces lower Cs content, which results in higher DMA selectivity. Although ion exchange of ammonium for $K^+$, $Sr^{2+}$ and ions in the ZK-5 may be incomplete in any given experiment, (typically leaving 0.1–0.5K ions per unit cell for the K, Sr form, and 1–5 Cs ions per unit cell for the K, Cs form), the product of ion-exchange is referred to herein as $NH_4$—ZK-5 or ammoniated ZK-5. Similarly, although deammoniation of $NH_4$—ZK-5 may not result in complete conversion of all $NH_4^+$ sites to $H^+$ or other sites, particularly when a sample is calcined at lower temperatures, the resulting product is referred to herein as zeolite H—ZK-5. Likewise, the zeolite rho after ammoniation is referred to as $NH_4^+$-rho, and after calcination as H-rho. The ease of ion exchange is a relative comparison which measures the number of exchanges needed for maximum exchange of the $K^+$ and $Sr^{2+}$, or $K^+$ and $Cs^+$, ions prior to calcination.

Identification of the two forms of ZK-5 and the rho is generally made by X-ray powder diffraction. The integrated intensities of the observed X-ray peaks can be used as a measure of zeolite crystallinity. High intensities indicate a highly crystalline product, while low intensities indicate less crystalline material. However, as crystalline size falls below about 50 nm, X-ray diffraction peaks broaden (H. P. Klug and L. E. Alexander, X-Ray Diffraction Techniques, Wily-Inter-science, New York, 1974). When crystallite size falls below about 2–6 nm, the peaks become so broad that they are difficult to detect by conventional analog recording spectrometers.

However, despite a lack of measurable X-ray peaks intensity, such "X-ray amorphous" zeolite crystallites are capable of shape selective catalysis (Jacobs et al., J. Chemical Society, Chemical Communications, p. 591 (1981)). For such crystallites, zeolite crystallinity is evident from infra-red spectra, sorption measurements, and catalytic shape selectivity. The acidic ZK-5 zeolites of this invention can be highly crystalline, poorly crystalline, or X-ray amorphous crystallites.

Generally, calcination temperatures must be sufficiently high to convert substantially all $NH_4^+$ sites to $H^+$ or other acid sites, yet not high enough to render significant amounts of the zeolite amorphous. The presence of $NH_4^+$ in a given sample can be determined by infra-red measurements. Excessive calcination can lead to collapse of zeolite crystalline structure and an amorphous state, which is to be distinguished from the "X-ray amorphous" zeolitic materials described above. The "X-ray amorphous" zeolites are obtained by limiting crystallization times, so that very small zeolite crystallites result. These crystallites exhibit characteristic zeolite selectivity, but permit rapid ingress of reactant molecules and egress of product molecules due to their small size.

Process Conditions

As previously noted, the process of the present invention comprises reacting methanol and/or dimethylether (DME) and ammonia, in amounts sufficient to provide a carbon/nitrogen (C/N) ratio from about 0.2 to about 1.5, in the presence of acidic zeolite ZK-5 (prepared from K, Sr), at a temperature from about 250° C. to about 450° C. Reaction pressures can be varied from 1–1000 psi (7–7000 kPa) with a methanol/DME space time of 0.01 to 80 hours. The resulting conversion of methanol and/or DME to methylamines is generally in excess of 85% (on a mole basis) and to dimethylamine is generally greater than 40%. In addition, the selectivity to and yield of trimethylamine is suppressed. Thus molar yields of dimethylamine generally exceed 40% and molar yields of trimethylamine generally are less than 30%, under the process conditions of the present invention.

The process variables to be monitored in practicing the process of the present invention include C/N ratio, temperature, pressure, and methanol/DME space time. The latter variable is calculated as the mass of catalyst divided by the mass flow rate of methanol and DME introduced to a process reactor (mass catalyst/mass methanol+DME fed per hour.)

Generally, if process temperatures are too low, low conversion of reactants to dimethylamine and monomethylamine will result. Increases in process temperatures will ordinarily increase catalytic activity, however, if temperatures are excessively high, equilibrium conversions and catalyst deactivation can occur. Preferably, reaction temperatures are maintained between 300° C. and 400° C. with lower temperatures within this range essentially preferred in order to minimize catalyst deactivation. At relatively low pressures, products must be refrigerated to condense them for further purification adding cost to the overall process. However, excessively high pressures require costly thick-walled reaction vessels. Preferably, pressures are maintained at 10–500 psi (70–3000 kPa). Short methanol/DME space times result in low conversions and tend to favor the production of monomethylamine. Long methanol space times may result either in inefficient use of catalyst or production of an equilibrium distribution of the products at very high methanol/DME conversions. Generally, methanol/DME space times of 0.01–80 hours are satisfactory, with methanol/DME space times of 0.10–1.5 hours being preferred (corresponding to methanol/DME space velocities of 0.013–100 g methanol+DME/g of catalyst/hour, preferably 0.67–10 g of methanol+DME/g of catalyst/hour).

The molar reactant ratio of methanol and/or dimethylether to ammonia, herein expressed as the C/N ratio (g atoms C/g atoms N), is critical to the process of the present invention. As the C/N ratio is decreased, production of monomethylamine is increased. As the C/N ratio is increased, production of trimethylamine increases. Catalyst deactivation is also greater at high C/N ratios. Accordingly, for best results, C/N ratios should be maintained between 0.2 and 1.5, and preferably from 0.5 to 1.2 in conducting the process of the present invention.

The efficiency of the process of the invention is measured by overall conversion of methanol and/or DME to methylamines, and by selectivity of dimethylamine production. For example, if methanol is used as the sole reactant, overall conversion is determined by comparison of the amount (in moles) of methanol in the product mixture, which is considered to be unconverted, to the amount in the reactant feed. Thus, overall conversion in percent is given by:

$$100 \left( 1 - \frac{\text{Moles MeOH in product}}{\text{Moles MeOH in Feed}} \right)$$

Conversion of methanol to methylamines, in percent is given by:

$$100 \left( 1 - \frac{\text{Moles MeOH in Prod.} + 2(\text{Moles DME in Prod})}{\text{Moles MeOH in Feed}} \right)$$

Conversion of methanol to monomethylamine (MMA) in percent, is given by:

$$100 \left( \frac{\text{Moles MMA}}{\text{Moles MeOH in Feed}} \right)$$

Similarly, conversion of methanol to dimethylamine (DMA), in percent, is given by:

$$100 \left( \frac{2(\text{Moles DMA})}{\text{Moles MeOH in Feed}} \right)$$

and conversion of methanol to trimethylamine (TMA), in percent, is given by:

$$100 \left( \frac{3(\text{Moles TMA})}{\text{Moles MeOH in Feed}} \right)$$

Finally, selectivity to DMA is calculated by analysis of product composition. Thus, selectivity to DMA, in percent, is provided by the following expression:

$$100\left(\frac{\text{Moles DMA}}{\text{Moles MMA + Moles TMA + Moles DMA + Moles DME}}\right)$$

For efficient operation, the catalyst must be selective at high conversion (87-98%) and a C/N ratio of 0.5-1.2.

In practicing the process of the invention, the zeolite catalyst can be combined with another material resistant to the temperature and other conditions employed in the process. Such matrix materials include synthetic or natural substances such as clays, silica, and metal oxides.

Comparison of selectivities for different samples should be made at similar conversions since selectivity varies with conversion. At low conversions, MMA production is favored; at very high conversions, the reaction will approach an equilibrium distribution and thus result in increased TMA production.

As discussed earlier, selectivities can be further improved by modifying the catalyst with a coating, an example of which is described in Bergna et al., U.S. Pat. Nos. 4,683,334 and 4,752,596, incorporated by reference herein. Specifically, to improve selectivity, coating of H—ZK-5 prepared from K, Sr can be accomplished in the following manner: (1) a sample of the catalyst is exposed to the ambient atmosphere and is immersed in tetraethylorthosilicate (TEOS) for 2 hours; (2) the sample is filtered and dried at 23° C. overnight; (3) the sample is then heated in flowing nitrogen at 550° C. for 3 hours. The preceding treatment can be performed with one or more compounds containing at least one element selected from silicon, aluminum, boron and phosphorous, to deposit substantially on the external surfaces of the H—ZK-5 at least 0.05 weight % of the element.

In summary, the invention provides a process for producing methylamines using the K, Sr—ZK-5 which yields improved selectivity to DMA and MMA, and reduced selectivity to TMA and DME when compared to K, Cs—ZK-5. As shown in Table I below, the selectivity to the less desirable component, TMA, for the K, Sr—ZK-5 is 1% or 6 times lower than the best performance of the comparative sample A, prepared from K, Cs—ZK-5. This represents a significant commercial advantage when market conditions demand little or no TMA. Also, this reduction in TMA greatly reduces the load on the separation column that separates the methylamine products in processing. Further, in preparing the catalyst, the ease of ion exchange is greatly enhanced, as fewer exchanges are needed for maximum exchange of ions prior to calcination. An additional advantage of the K, Sr—ZK-5 includes improved economic incentive, the K, Sr—ZK-5 representing a cost approximately ½ that of K, Cs—ZK-5.

The process of the present invention can be further understood by reference to the following Examples, wherein all temperatures are expressed in degrees Celsius (°C.) and all percentages are by weight unless otherwise indicated. In composition determinations, it was assumed that there were 192 oxygen atoms per unit cell. Analysis determined the relative amounts of the various cations present, and remaining positively-charged species were assumed to be hydrogen.

EXAMPLE 1

Preparation of K, Sr—ZK-5 and Its Use in Methylamines Reaction

Zeolite H—ZK-5 was prepared generally according to the method of Verduijn, U.S. Pat. No. 4,994,249. The first step in preparation was to dissolve 9.7 g of Al-$(OH)_3$ in 18 g of hot KOH. Second, 1.7 g of $Sr(OH)_2 \cdot 8-H_2O$ were dissolved in hot water and the two mixtures were then combined. The addition of $SiO_2$ yielded a stiff gel which was transferred to a Teflon ® bottle. The mixture was then heated at autogenous pressure at 150° C. for 91 hours. Afterwards, the product was filtered, washed with $H_2O$ and dried. An X-ray diffraction pattern obtained for this material was in agreement with that provided by the disclosure of Verduijn, U.S. Pat. No. 4,994,249.

The product was exchanged six times with 10% $NH_4NO_3$ solution, 10 ml solution/g zeolite, at 90° C. for one hour periods. The product was separated from the solution after each exchange, fresh $NH_4NO_3$ being used for each exchange. The crystals were then dried overnight at 100° C. Analysis yielded a unit cell of $K_{0.2}(NH_4)_{19.8}Si_{76.0}Al_{20.0}O_{192}$. Calcination was performed in a 1 inch deep (2.5 cm) bed at 500° C. for 8 hours in an oven. The result is the acidic zeolite H—ZK-5.

Before use in the reactor, the zeolite was pressed into pellets at 20000 PSI, then crushed and sieved to pass sieve No. 20 ASTM standard, but not to pass sieve No. 40 ASTM standard. One gram of the resulting catalyst was placed in a stainless steel U-tube reactor 0.25 in (0.64 cm) in diameter and 18 to 20 in (45.7–50.8 cm) length. First, the reactor was heated to reaction temperature in a fluidized sand bath. The reaction pressure was maintained at 200 psi to parallel commercial production conditions. Reactants methanol and ammonia were fed to a pre-heater at a molar ratio of about 1, vaporized and then passed through the reactor into contact with the catalyst sample. Space times (g catalyst/(g methanol+DME fed per hour)) were varied between 42.2 and 5.3 minutes. The reactor effluent was continuously analyzed by gas chromatagraphy for ammonia, dimethylether (DME), methanol, water, and mono-, di-, and trimethylamine. The percentage selectivities of conversion to each methylamine species, as well as DME, are given in Table I, below, reported at 90% methanol conversion.

TABLE I

| | | Catalyst Molar Selectivities at 90% Methanol Conversion | | | | | | | |
|---|---|---|---|---|---|---|---|---|---|
| Ex. | Catalyst Precursor | Calc. Temp°C. | Reaction Temp. | Reaction Press PSI | MMA % | DMA % | Combined MMA + DMA | TMA % | DME % |
| 1 | K,Sr-ZK-5 | 500 | 325 | 200 | 40 | 59 | 99 | 1 | 0 |
| A | K,Cs-ZK-5 | 500 | 325 | 200 | 34 | 52 | 86 | 13 | 1 |
|   | K,Cs-ZK-5 | 500 | 300 | 200 | 30 | 62 | 92 | 6 | 2 |
| B | Na—Cs Rho | 600 | 300 | 200 | 32 | 64 | 96 | 4 | 0 |

Comparative Example A

K, CS—ZK-5 Preparation and Its Use in Methylamines Reaction

Zeolite K, Cs–ZK-5 was prepared substantially according to the procedure set forth in Example 3 of Robson, U.S. Pat. No. 3,720,753. A mixture of 53 g KOH, 36 g CsOH and 90 g $H_2O$ was heated to 100° C. at which point 39 g of $Al(OH)_3$ was added. The mixture was cooled to room temperature and 295 g of colloidal silica (Ludox® HS-40) was added in a polypropylene container to form 500 ml. The sample was then heated for 5 days, washed 4 times with 1000 ml $H_2O$ and dried at 110° C.

The product was exchanged in the same manner as described in Example 1, except 12 exchanges with 10% $NH_4NO_3$ were made instead of 6. Analysis yielded a unit cell of $K_{0.6}Cs_{2.1}(NH_4)_{19.3}Si_{73.9}Al_{22.1}O_{192}$. Calcination was performed in a 1 inch deep (2.5 cm) bed at 500° C. for 8 hours in an oven. The result is the acidic zeolite H—ZK-5. An X-ray diffraction pattern obtained for the resulting product is similar to that indicated in the patent for K, Cs—ZK-5.

The sample was then evaluated for catalytic performance by a procedure substantially similar to that described for Example 1, at reaction temperatures of 300° C. and 325° C. The results, which are displayed in Table I, illustrate the comparative catalyst selectivities.

Comparative Example B

Zeolite Rho Use in Methylamines Reaction

Zeolite Rho was prepared substantially according to the procedure set forth in Robson, U.S. Pat. No. 3,904,738. The catalyst was calcined in a ½ inch deep (1.3 cm) bed at 600° C. The sample was then evaluated for catalytic performance by a procedure substantially similar to that described for Example 1. The results, which are displayed in Table I, illustrate the comparative catalyst selectivities.

We claim:

1. An improved process for producing dimethylamine and monomethylamine comprising:
    contacting methanol and/or dimethylether and ammonia, in amounts sufficient to provide a carbon/nitrogen ratio from about 0.2 to about 1.5 and at a reaction temperature from about 250° C. to about 450° C., in the presence of a catalytic amount of an acidic zeolite H—ZK-5;
    wherein the improvement comprises using an acidic zeolite H—ZK-5 which has been obtained by ion exchange of K,Sr—ZK-5.

2. The process of claim 1, wherein said acidic zeolite H—ZK-5 has been prepared from K,Sr—ZK-5 in a process comprising the steps of:
    (a) performing an ion exchange reaction between the $K^+Sr^{2+}$ ions of the K,Sr—ZK-5 and $NH_4^+$ ions, to yield $NH_4$—ZK-5; and
    (b) calcining the $NH_4$—ZK-5 of step (a) at a temperature of about 400° C. to about 700° C., to yield H—ZK-5.

3. The process of claim 1, wherein the H—ZK-5 has been modified by treatment with one or more compounds containing at least one element selected from the group consisting of silicon, aluminum, phosphorous, and boron, to deposit thereon at least 0.05 weight percent of the element.

4. The process of claim 1, wherein the reaction temperature is from about 300° C. to about 400° C.

5. The process of claim 1, wherein the reaction pressures are from about 10 to about 500 psi.

6. The process of claim 1, wherein the carbon/nitrogen ratio is from about 0.5 to about 1.2.

7. The process of claim 2, wherein at step (b) the calcining temperature is from about 500° C. to about 600° C.

* * * * *